United States Patent [19]

Sherman

[11] Patent Number: 5,690,962
[45] Date of Patent: *Nov. 25, 1997

[54] STABLE SOLID FORMULATION OF ENALAPRIL SALT AND PROCESS FOR PREPARATION THEREOF

[75] Inventor: Bernard Charles Sherman, Willowdale, Canada

[73] Assignee: Apotex Corporation, Buffalo Grove, Ill.

[*] Notice: The term of this patent shall not extend beyond the expiration date of Pat. No. 5,573,780.

[21] Appl. No.: 711,826

[22] Filed: Sep. 10, 1996

Related U.S. Application Data

[63] Continuation of Ser. No. 511,297, Aug. 4, 1995, Pat. No. 5,573,780.

[51] Int. Cl.$^6$ ................................ A61K 9/14; A61K 9/16
[52] U.S. Cl. .................... 424/489; 424/464; 514/777; 514/970
[58] Field of Search ..................... 424/464, 465, 424/489

[56] References Cited

U.S. PATENT DOCUMENTS

| | | | |
|---|---|---|---|
| 4,374,829 | 2/1983 | Harris et al. | 424/177 |
| 4,743,450 | 5/1988 | Harris et al. | 424/440 |
| 5,350,582 | 9/1994 | Merslavic et al. | 424/464 |
| 5,573,780 | 11/1996 | Sherman | 424/464 |

*Primary Examiner*—James M. Spear
*Attorney, Agent, or Firm*—Caesar, Rivise, Bernstein, Cohen & Pokotilow, Ltd.

[57] ABSTRACT

There is disclosed a stable pharmaceutical solid composition comprising enalapril as the sodium salt, which is made by the steps of:

i) mixing enalapril maleate with a carrier, an alkaline sodium compound, and water
ii) drying the wet mass, and;
iii) further processing the resultant dried mass into tablets.

When the water is added in the aforesaid process, an acid-base reaction occurs which converts the enalapril maleate into the more stable enalapril sodium salt.

8 Claims, No Drawings

STABLE SOLID FORMULATION OF ENALAPRIL SALT AND PROCESS FOR PREPARATION THEREOF

BACKGROUND OF THE INVENTION

This application is a continuation of Ser. No. 08/511,297 filed Aug. 4, 1995 now U.S. Pat. No. 5,573,780.

U.S. Pat. No. 4,374,829 discloses the compound enalapril maleate, which is a drug useful to treat hypertension. This patent also discusses methods of formulating drugs into pharmaceutical compositions such as tablets and capsules, but discloses no example of a tablet or capsule containing specifically enalapril maleate.

In order to manufacture pharmaceutical tablets, it is necessary to mix the active ingredient with inactive ingredients which may serve as binders, fillers, disintegrating agents, lubricants, and colorants or have other purposes. Inactive ingredients are also known as "excipients".

The final mixture of active ingredient and excipients is made into tablets on a tablet press. The processes of preparing the mixture and making tablets are well known to those skilled in the art of pharmaceutical formulation.

One of the requirements for an acceptable pharmaceutical composition is that it must be stable, so as not to exhibit substantial decomposition of the active ingredient during the time between manufacture of the composition and use by the patient. Surprisingly, it has been found that enalapril maleate is not compatible with most of the usual excipients, including most of those mentioned in U.S. Pat. No. 4,374,829. Decomposition of enalapril maleate is accelerated by most of these excipients, thus making it very difficult to formulate a stable tablet containing enalapril maleate.

The difficulty of formulating a stable tablet containing enalapril maleate is confirmed by European patent application number 92119896.6. That application discloses that a stable formulation can be made by suspending enalapril maleate in water, and adding an alkaline sodium compound, whereupon an acid-base reaction occurs to convert the enalapril maleate into enalapril sodium salt (hereinafter referred to as "enalapril sodium") plus maleic acid sodium salt, thereby forming a clear solution. Other excipients are then added the mixture is dried, and the dry powder processed into tablets. Stability data contained in this patent application demonstrates that the final composition containing enalapril sodium mixed with maleic acid sodium salt and other ingredients is more stable than a similar composition containing enalapril maleate.

However, the formulations of European application 92119896.6 have the disadvantage of requiring the step of suspending the enalapril maleate in water, adding the alkaline sodium compound, and mixing until the acid-base reaction is complete.

This requires the use of more equipment than would otherwise be needed for the manufacture of tablets. Also, because the enalapril sodium is in aqueous solution during the process, significant hydrolysis can occur by which some enalaprilat is formed, thus reducing the purity of the product.

U.S. patent application Ser. 08/276,678, U.S. Pat. No. 5,562,921 discloses that stable tablets comprising enalapril maleate can be made if excipients are restricted to certain those which do not to cause decomposition. However, this approach limits the excipients that can be used, making it difficult to produce tablets exhibiting good hardness. In light of the foregoing, the object of the invention is to enable production of tablets through a process whereby enalapril maleate is converted to the more stable sodium salt without requiring the steps of suspending the enalapril maleate in water, adding the alkaline sodium compound, and mixing until the reaction is complete and a clear solution is formed.

SUMMARY OF THE INVENTION

It has surprisingly been found that enalapril maleate can be converted to the stable enalapril sodium salt by mixing the enalapril maleate with an alkaline sodium compound and other excipients in dry form, adding sufficient water to moisten same, and thereafter drying, thus avoiding the need to suspend the enalapril maleate in water and to produce a solution of enalapril sodium in water.

The invention thus comprises the steps of:

i. Mixing enalapril maleate with an alkaline sodium compound and at least one other excipient which acts as a diluent or carrier.

ii. Adding water and mixing.

iii. Drying the wet mass.

iv. Adding a lubricant and optionally other ingredients.

v. Compression into tablets on a tablet press.

In the alternative, the alkaline sodium compound can be omitted from the initial mix of powders and instead dissolved in the water.

DETAILED DESCRIPTION OF THE INVENTION

As aforesaid, the invention enables production of tablets containing enalapril sodium by a process in which enalapril maleate is converted to enalapril sodium and maleic acid sodium salt without suspending the enalapril maleate in water and without converting the enalapril maleate to a clear solution of enalapril sodium and maleic acid sodium salt in water.

The molecular formula for enalapril maleate is $C_{20}H_{28}N_2O_5C_4H_4O_4$ and the molecular weight is 492.53.

The molecular equations for converting enalapril maleate to enalapril sodium plus disodium maleate using, as the alkaline sodium compound, one of sodium hydroxide, sodium carbonate, and sodium bicarbonate are as follows:

I) Using sodium hydroxide:

$$C_{20}H_{28}N_2O_5 \cdot C_4H_4O_4 + 3NaOH \rightarrow C_{20}H_{27}N_2O_5Na + Na_2C_4H_2O_4 + 3H_2O$$

ii) Using sodium carbonate:

$$2\,C_{20}H_{28}N_2O_5 \cdot C_4H_4O_4 + 3Na_2CO_3 \rightarrow 2\,C_{20}H_{27}N_2O_5Na + 2\,Na_2C_4H_2O_4 + 3H_2O + 3CO_2$$

iii) Using sodium bicarbonate:

$$C_{20}H_{28}N_2O_5 \cdot C_4H_4O_4 + 3NaHCO_3 \rightarrow C_{20}H_{27}N_2O_5Na + 2Na_2C_4H_2O_4 + 3H_2O + 3CO_2$$

It can be seen that a complete conversion of enalapril maleate to enalapril sodium plus disodium maleate requires, for each mole (492.53 g) of enalapril maleate, the following:

I) If sodium hydroxide is used, 3 moles, which is 120.0 g.

ii) If sodium carbonate is used, 1.5 moles, which is 159.0 g.

iii) If sodium bicarbonate is used, 3 moles, which is 252.0 g.

Per gram of enalapril maleate, the amounts required are thus 0.244 g of sodium hydroxide, 0.323 g of sodium carbonate, or 0.512 g of sodium bicarbonate.

The present invention contemplates converting the enalapril maleate to enalapril sodium plus sodium maleate by either:

a) Mixing the enalapril maleate with an alkaline sodium compound and at least one other excipient as a diluent or carrier and adding water and mixing, or b) mixing enalapril maleate with a least one excipient (other than the alkaline sodium compound) as a diluent or carrier, adding a solution of the alkaline sodium compound in water and mixing.

Among excipients suitable as diluents or carriers are lactose (either anhydrous or monohydrate), cellulose, starch, calcium phosphates, mannitol and many others well known in the art. Especially preferred is lactose.

It will be understood that the alkaline sodium compound may be sodium hydroxide or a sodium salt of weak acid that will undergo an acid-base reaction with enalapril maleate in the presence of water. The alkaline sodium compound is preferably selected from sodium hydroxide, sodium carbonate, or sodium bicarbonate.

In either case a) or b), upon addition of the water or the solution of the alkaline sodium compound in water, the acid-base reaction will commence which converts the enalapril maleate to enalapril sodium plus disodium maleate, and also generates more water, and also carbon dioxide if either sodium carbonate or sodium bicarbonate is used as the sodium source.

In either case a) or b), the wet mass is then dried, which may be done in an oven, or in a fluid bed drier or other similar equipment.

It has been found that so long as the amount of water used is sufficient to render the mass very moist, the acid-base reaction will occur rapidly and will be complete or essentially complete before the drying of the mass in the subsequent drying process is completed.

After the mass is dried, it will preferably be passed through a screen to break any lumps and convert it to a free flowing powder.

This free flowing powder is then preferably processed as follows to make it into tablets. Firstly, it is remixed in dry form with a quantity of a lubricant to avoid sticking to the tooling in the subsequent tabletting process. Then it is made into tablets of required unit weight on a tablet press.

The lubricant will preferably be a metal stearate and most preferably magnesium stearate.

It will be understood that other excipients may optionally be added either to the initial powder mix, before it is wetted with the water or the solution of the alkaline sodium compound, or to the final powder mix before tabletting. Such further excipients may include for example, colouring agents (such as iron oxides), and disintegrants (such as starch) to speed the disintegration of the tablets after ingestion to ensure rapid release of the drug.

Tablets are thus made which contain enalapril as the sodium salt.

The invention will be further understood from the following examples which are intended to be illustrative but not limiting of the invention.

EXAMPLE 1

The following were mixed together:

| ENALAPRIL MALEATE | 50.0 g |
| LACTOSE MONOHYDRATE POWDER | 1660.0 g |

12.2 g of sodium hydroxide was then dissolved in 400 g of water, the solution was added to the foregoing powder, and the resultant wet mass was mixed well. The wet mass was then dried overnight in a drying oven at 50° C. The dried mass was then passed through a #40 screen to break any lumps, and the following was added:

| STARCH | 75.0 g |
| MAGNESIUM STEARATE | 8.3 g |

The material was mixed again, and then compressed into tablets at a weight of 180 mg per tablet.

The total weight of materials used in this example, other than the water, is 1805.5 g. However, the reaction of the enalapril maleate with the sodium hydroxide produced about 5.5 g of additional water which was then lost when the material was dried in the oven.

On a dried basis, 50 g of enalapril maleate was thus used to make 1800 g of final mix. A tablet with 180 mg weight thus contains enalapril sodium equivalent to 5 mg of enalapril maleate.

EXAMPLE 2

The following were mixed together:

| ENALAPRIL MALEATE | 100.0 g |
| LACTOSE MONOHYDRATE POWDER | 1600.0 g |
| RED IRON OXIDE | 5.0 g |

The red iron oxide was included as a colouring agent. To ensure uniformity of colour, the mixed powder was then passed through a #40 screen and remixed.

32.3 g of sodium carbonate was then dissolved in 400 g of water, the solution was added to the foregoing powder, and the resultant wet mass was mixed well. The wet mass was then dried overnight in a drying oven at 50° C. The dried mass was then passed through a #40 screen to break any lumps, and the following as added:

| STARCH | 73.0 g |
| MAGNESIUM STEARATE | 8.6 g |

The material was then mixed again, and then compressed into tablets at a weight of 180 mg per tablet.

The total weight of materials used in this example, other than the water, is 1818.9 g. However, the reaction of the enalapril maleate with sodium carbonate produced about 13.4 g of carbon dioxide and 5.5 g of additional water. The carbon dioxide was lost to the atmosphere and the additional water was lost when the material was dried in the oven.

On a dried basis, 100 g of enalapril maleate was thus used to make 1800 g of final mix. A tablet with 180 mg weight thus contains enalapril sodium equivalent to 10 mg of enalapril maleate.

EXAMPLE 3

The following were mixed together:

| ENALAPRIL MALEATE | 50.0 g |
| SODIUM BICARBONATE | 25.6 g |
| LACTOSE MONOHYDRATE POWDER | 1650.0 g |

400 g of water was then added to the foregoing mixed powder, and the resultant wet mass was mixed well. The wet mass was then dried overnight in a drying oven at 50° C. The dried mass was then passed through a #40 screen to break any lumps, and the following was added:

| | |
|---|---|
| STARCH | 75.0 g |
| MAGENSIUM STEARATE | 8.8 g |

The material was mixed again, and then compressed into tablets at a weight of 180 mg per tablet.

The total weight of materials used in this example, other than water, is 1809.4 g. However, the reaction of the enalapril maleate with the sodium bicarbonate produced about 6.7 g of carbon dioxide and 2.7 g of additional water. The carbon dioxide was lost to the atmosphere and the additional water was lost when the material was dried in the oven.

On a dried basis, 50 g of enalapril maleate was thus used to make 1800 g of final mix. A tablet with 180 mg weight thus contains enalapril sodium equivalent to 5 mg of enalapril maleate.

What is claimed:

1. A process of manufacture of a pharmaceutical solid composition comprising enalapril sodium, which process comprises the steps of:
   i)
      a) mixing enalapril maleate with an alkaline sodium compound and at least one other excipient, adding water sufficient to moisten, and mixing to achieve a wet mass, or
      b) mixing enalapril maleate with at least one excipient other than an alkaline sodium compound, adding a solution of an alkaline sodium compound in water, sufficient to moisten and mixing to achieve a wet mass; thereby to achieve a reaction without converting the enalapril maleate to a clear solution of enalapril sodium and maleic acid in water.
   ii) drying the wet mass, and
   iii) further processing the dried material into a pharmaceutical solid composition.

2. A process as in claim 1 wherein the alkaline sodium compound is selected from sodium hydroxide, sodium carbonate and sodium bicarbonate.

3. A process as in claim 1 or 2 wherein the excipient is lactose.

4. A process as in claim 1 which further comprises addition of a lubricant.

5. A process as in claim 4 wherein the lubricant is a metal stearate.

6. A process as in claim 5 wherein the metal stearate is magnesium stearate.

7. A process as in claims 1 which further comprises the addition of a disintegrant.

8. A process as in claim 7 wherein the disintegrant is starch.

* * * * *